United States Patent

Eljamal et al.

[11] Patent Number: 5,993,783
[45] Date of Patent: Nov. 30, 1999

[54] METHOD AND APPARATUS FOR PULMONARY ADMINISTRATION OF DRY POWDER α1-ANTITRYPSIN

[75] Inventors: Mohammed Eljamal, San Jose; John S. Patton, San Carlos, both of Calif.

[73] Assignee: Inhale Therapeutic Systems, San Carlos, Calif.

[21] Appl. No.: 09/114,713

[22] Filed: Jul. 13, 1998

Related U.S. Application Data

[63] Continuation of application No. 08/617,512, Mar. 13, 1996, Pat. No. 5,780,014.

[51] Int. Cl.⁶ ......................................................... A61K 9/12
[52] U.S. Cl. .................................................. 424/46; 424/45
[58] Field of Search ................................... 424/45, 46, 43; 514/373

[56] References Cited

U.S. PATENT DOCUMENTS

| | | |
|---|---|---|
| 2,598,525 | 5/1952 | Fox . |
| 3,362,405 | 1/1968 | Hazel . |
| 3,425,600 | 2/1969 | Abplanalp . |
| 3,921,637 | 11/1975 | Bennie et al. . |
| 3,964,483 | 6/1976 | Mathes . |
| 3,991,304 | 11/1976 | Hillsman . |
| 3,991,761 | 11/1976 | Cocozza . |

(List continued on next page.)

FOREIGN PATENT DOCUMENTS

| | | |
|---|---|---|
| 0 237 507 | 9/1987 | European Pat. Off. . |
| 0 289 336 | 4/1988 | European Pat. Off. . |
| 0 347 779 | 12/1989 | European Pat. Off. . |
| 0 467 172 | 1/1992 | European Pat. Off. . |
| 0 468 914 | 1/1992 | European Pat. Off. . |
| 0 490 797 | 6/1992 | European Pat. Off. . |
| 0 506 293 | 9/1992 | European Pat. Off. . |
| 2257351 | 8/1975 | France . |
| 7712041 | 5/1979 | Netherlands . |
| 0628930 | 9/1978 | U.S.S.R. . |
| 1003926 | 3/1983 | U.S.S.R. . |
| 1527605 | 10/1978 | United Kingdom . |
| 88/04556 | 6/1988 | WIPO . |
| 90/07351 | 7/1990 | WIPO . |
| 90/09780 | 9/1990 | WIPO . |
| 90/15635 | 12/1990 | WIPO . |
| 91/02545 | 3/1991 | WIPO . |
| 91/02558 | 3/1991 | WIPO . |
| 93/02712 | 2/1993 | WIPO . |
| 93/09832 | 5/1993 | WIPO . |
| 94/08552 | 4/1994 | WIPO . |
| 96/01105 A1 | 6/1995 | WIPO . |

OTHER PUBLICATIONS

Gennaro, A.R. (1985). Remington's Pharmaceutical Science, Mack Pub. Co. pp. 1670–1677.
Morén, F. et al. (1993). Aerosols in Medicine: Principles, Diagnosis and Therapy, Elsevier, pp. 303–319.
Health News Daily (1995), vol. 7, Issue 13 Jan. Issue.
Björk, "Degradable Starch Microspheres as a Nasal Delivery System for Insulin," *Int'l J. of Pharmac.*, 47:233–238 (1988).
Bohnet, "Dalculation and Design of Gas/Solid–Injectors," *Powder Technology*, pp. 302–313 (1984).
Budrik et al., "Ejector Feeders for Pneumatic Transport Systems," *Dhemical and Petroleum Engineering*, 14(9–10) (1978).
Byron et al., "Drug Delivery via the Respiratory Tract," *J. Aerosol Medicine*, 7(1):49–75 (1994).

(List continued on next page.)

*Primary Examiner*—Raj Bawa
*Attorney, Agent, or Firm*—Townsend and Townsend and Crew LLP

[57] ABSTRACT

Dry powders of α1-antitrypsin are administered pulmonarily to patients to treat, for example, certain types of emphysema. The dry powder compositions may comprise aggregates of fine particles, which aggregates are friable and break-up upon dispersion in a flowing gas stream. Typically, the dispersed powders are captured in a chamber and subsequently inhaled by a patient for pulmonary treatment of emphysema and other conditions.

46 Claims, 3 Drawing Sheets

U.S. PATENT DOCUMENTS

| | | |
|---|---|---|
| 3,994,421 | 11/1976 | Hansen . |
| 4,036,223 | 7/1977 | Obert . |
| 4,069,819 | 1/1978 | Valentini et al. . |
| 4,098,273 | 7/1978 | Glenn . |
| 4,153,689 | 5/1979 | Hiral et al. . |
| 4,249,526 | 2/1981 | Dean et al. . |
| 4,253,468 | 3/1981 | Lehmbeck . |
| 4,294,829 | 10/1981 | Suzuki et al. . |
| 4,338,931 | 7/1982 | Cavazza . |
| 4,446,862 | 5/1984 | Baum et al. . |
| 4,452,239 | 6/1984 | Malem . |
| 4,484,577 | 11/1984 | Sackner et al. . |
| 4,503,035 | 3/1985 | Pestka et al. . |
| 4,534,343 | 8/1985 | Nowacki et al. . |
| 4,599,311 | 7/1986 | Kawasaki . |
| 4,624,251 | 11/1986 | Miller . |
| 4,627,432 | 12/1986 | Newell et al. . |
| 4,649,911 | 3/1987 | Knight et al. . |
| 4,677,975 | 7/1987 | Edgar et al. . |
| 4,698,328 | 10/1987 | Neer et al. . |
| 4,739,754 | 4/1988 | Shaner . |
| 4,790,305 | 12/1988 | Zoltan et al. . |
| 4,807,814 | 2/1989 | Douche et al. . |
| 4,811,731 | 3/1989 | Newell et al. . |
| 4,819,629 | 4/1989 | Jonson . |
| 4,823,784 | 4/1989 | Bordoni et al. . |
| 4,833,125 | 5/1989 | Neer et al. . |
| 4,884,565 | 12/1989 | Cocozza . |
| 4,889,114 | 12/1989 | Kladders . |
| 4,907,583 | 3/1990 | Wetterlin et al. . |
| 4,926,852 | 5/1990 | Zoltan et al. . |
| 4,942,544 | 7/1990 | McIntosh et al. . |
| 4,968,607 | 11/1990 | Dower et al. . |
| 4,984,158 | 1/1991 | Hillsman . |
| 4,995,385 | 2/1991 | Valentini et al. . |
| 5,011,678 | 4/1991 | Wang et al. . |
| 5,027,806 | 7/1991 | Zoltan et al. . |
| 5,033,463 | 7/1991 | Cocozza . |
| 5,035,237 | 7/1991 | Newell et al. . |
| 5,048,514 | 9/1991 | Ramella . |
| 5,049,388 | 9/1991 | Knight et al. . |
| 5,081,228 | 1/1992 | Dower et al. . |
| 5,093,316 | 3/1992 | Lezdey et al. . |
| 5,099,833 | 3/1992 | Michaels . |
| 5,113,855 | 5/1992 | Newhouse . |
| 5,161,524 | 11/1992 | Evans . |
| 5,180,812 | 1/1993 | Dower et al. . |
| 5,186,164 | 2/1993 | Raghuprasad . |
| 5,204,108 | 4/1993 | Illum . |
| 5,230,884 | 7/1993 | Evans et al. . |
| 5,254,330 | 10/1993 | Ganderton et al. . |
| 5,295,479 | 3/1994 | Lankinen . |
| 5,302,581 | 4/1994 | Sarin et al. . |
| 5,309,900 | 5/1994 | Knoch et al. . |
| 5,320,094 | 6/1994 | Laube et al. . |
| 5,320,714 | 6/1994 | Brendel . |
| 5,331,953 | 7/1994 | Andersson et al. . |
| 5,354,562 | 10/1994 | Platz et al. . |
| 5,364,838 | 11/1994 | Rubsamen . |
| 5,376,359 | 12/1994 | Johnson . |
| 5,376,386 | 12/1994 | Ganderton et al. . |
| 5,466,701 | 11/1995 | Hlasta et al. . |
| 5,488,062 | 1/1996 | Dunlap et al. . |
| 5,641,510 | 6/1997 | Clark et al. . |
| 5,780,014 | 7/1998 | Eljamal et al. . |

OTHER PUBLICATIONS

Dhien et al., "Intranasal Drug Delivery for Systemic Medications," *DRD Dritical Reviews in Therapeutic Drug Darrier Systems*, 4(2):67–92 (1987).

Dolthorphe et al., "The Parmacokinetics of Pulmonary–Delivered Insulin: A Domparison of Intratracheal and Aerosol Admininstration to the Rabbit," *Pharmaceutical Research*, 9(6):764–768 (1992).

Duchateau et al., "Bile Salts and Intranasal Drug Absorption," *Int'l J. of Pharmac.*, 31:193–199 (1986).

Elliott et al., "Parenteral Absorption of Insulin from the Lung in Diabetic Dhildren," *Aust. Paediatr. J.*, 23:293–297 (1987).

Fox et al., "Performance of a Venturi Eductor as a Feeder in a Pneumatic Donveying System," *Powder and Bulk Engineering*, pp. 33–36 (1988).

Friedmann, "Progress Toward Human Gene Therapy," *Science*, 244:1275–1281 (1989).

Gansslen, "Uber Inhalation von Insulin," *Klin. Wochenschr.*, 4(71) (1925).

Habener et al., "Parathyroid Hormone: Secretion and Metabolism In Vivo," *PNAS*, 68(12):2986–2991 (1971).

Hastings, "Dlearance of Different–Sized Proteins from the Alveolar Space in Humans and Rabbits," *Amer. Physiol. Soc.*, pp. 1310–1316 (1992).

Hesch et al., "Puslatile Secretion of Parathyroid Hormone and its Action on a Type I and Type II PTH Receptor: A Hypothesis for Understanding Osteoporosis," *Dalcified Tissue International*, 42:341–344 (1988).

Laube et al., "Preliminary Study of the Efficacy of Insulin Aerosol Delivered by Oral Inhalation in Diabetic Patients," *JAMA* 269(16):2106–2109 (1993).

Lee et al., "Development of an Aerosol Dosage Form Dontaining Insulin," *J. Pharm. Sci.*, 65(4):567–572 (1976).

Liu et al., "Pulmonary Delivery of Free and Liposomal Insulin," *Pharm. Research*, 10(2):228–232 (1993).

Nagano et al., "New Method of Insulin Therapy: Transpulmonary Absorption o Insulin," *Jikeikai Med. J.*, 32(3):503–506 (1985).

Nagai et al., "Powder Dosage Form of Insulin for Nasal Administration," *J. of Dontrolled Release*, 1:15–22 (1984).

Neer et al., "The Use of Parathyroid Hormone Plus 1,25–Dihydroxyvitamin D to Increase Trabecular Bone in Osteoporotic Men and Postmenopausal Women," *Osteoporosis*, pp. 829–835 (1987).

Nieminen et al., "Aerosol Deposition in Automatic Dosimeter Nebulization," *European J. Resp. Dis.*, 71:145–152 (1987).

Patton et al., "Pulmonary Delivery of Peptides and Porteins for Systemic Action," *Adv. Drug Delivery Reviews*, 8:179–196 (1992).

Pikal, "Polymorphism in Pharmaceutical Solids," AAPS, Annual Meeting and Exposition, Nov. 15–19 (1992).

Pittman et al., "Pneumatic Donveying of Bluk Solids Using a Vacuum Aeroated Feed Nozzel," Solids Handling Donference, Paper D4, pp. D–41 to D–51 (1986).

Rao, "Aerosol Insulin Inhalation Enquiry," *Indian J. Physiol. Pharmacol.*, 3:161–167 (1959).

Rosenfeld et al., "Adenovirus–Mediated Transfer of a Recombinant α1–Antitrypsin Gene to the Lung Epithelium in Vivo," *Science*, 252:431–434 (1991).

Ryden et al., "Effect of Polymers and Microspheres on the Nasal Absorption of Insulin in Rats," *Int'l J. of Pharmac.*, 83:1–10 (1992).

Sakr, "A New Approach for Insulin Delivery via the Pulmonary Route: Design and Pharmacokinetics in Non–Diabetic Rabbits," *Int'l J. of Pharmac.*, 86:1–7 (1992).

Schlüler et al., (Abstract) Reproduction Form for Annual Meeting Program Published in Diabetes, 13(6):230–232 (1987).

Stribling et al., "The Mouse as a Model for Dationic Liposome–Based, Aerosolized Gene Delivery," *J. Biopharm. Sci.*, 3(1/2):255–263.

Underwood et al., "A Novel Technique for the Administration of Bronchodilator Drugs Formulated as Dry Powders to the Aneasthetized Guinea Pig," *J. Pharmac. Methods*, 26:203–210 (1991).

Wigley, "Insulin Across Respiratory Mucosae by Aerosol Delivery," *Diabetes*, 20(8):552–556.

Witham et al., "Dry Dispersion with Sonic Velocity Nozzels," Workshop on Dissemination Techniques for Smoke and Obscurants Dhemical Systems Laboratory, Aberdeen Proving Ground, MD, Mar. 14–16, 1983).

Yoshida, "Absorption of Insulin Delivered to Rabbit Trachea Using Aerosol Dosage Form," *J. Pharm. Sci.*, 68(5):670–671 (1979).

Zholob et al., "Effect of Injector Unit Design on the Particle Size of Atomized Powder," Translated from *Poroshkovaya Metallurgiya*, 6(198):13–16 (1979).

METHOD AND APPARATUS FOR PULMONARY ADMINISTRATION OF DRY POWDER α1-ANTITRYPSIN

This application is a continuation of, and claims the benefit of priority from application Ser. No. 08/617,512, filed on Mar. 13, 1996, now U.S. Pat. No. 5,780,014 the full disclosure of which is incorporated herein by reference.

BACKGROUND OF THE INVENTION

Neutrophil elastase is a broad spectrum protease that is known to have access to the tissues of the lung. This protease is generally capable of degrading all major protein components of the alveolar interstitium. The unrestrained action of this protease, with its elastolytic properties can lead to the destruction of lung connective tissue and to the anatomic and functional derangements of pulmonary emphysema. Smith, et al., J. Clin. Invest. 84:1145–1154 (1989).

α1-antitrypsin ("α1AT") is a protease inhibitor with inhibitory activity toward neutrophil elastase. A deficiency of α1-antitrypsin in the lower respiratory tract has been found to be central to the pathogenesis of emphysema due to the critical role of α1AT in protecting alveolar structures from neutrophil elastase. α1AT deficiency is a genetic disorder characterized by low plasma and lung levels of the inhibitor and the development of emphysema by the third to fourth decades.

In addition to genetic deficiencies in α1AT, it has been found that the lungs of cigarette smokers are burdened with neutrophils. In particular, significantly increased numbers of neutrophils have been found in cell suspensions isolated from bronchoalveolar lavage fluid and from open lung biopsies of both normal and sarcoid cigarette smokers compared with non-smokers. Hunnighake and Crystal, Am. Rev. Respir. Dis. 128:833–838 (1983).

Treatment methods for α1AT deficiency, whether genetic or acquired, have primarily focused around augmentation therapy, providing an exogenous source of α1AT to patients suffering from such a deficiency. Intravenous administration has been previously employed in this augmentation therapy to provide an exogenous source of α1AT. However, in order to provide effective concentrations of the inhibitor in the tissue where it is needed, e.g., lung tissue, intravenous methods require administration of large amounts of α1AT, e.g., 4 to 5 grams/week. Further, this intravenous administration generally must be carried out in a hospital setting.

Successful results have been reported using aerosol administration of liquid α1AT formulations. Aerosol administration provides local delivery of the inhibitor to the effected tissue of the lower respiratory tract, thereby requiring lower dosages. See, Published European Patent Application No. 0 289 336, Smith et al., J. Clin. Invest. 84:1145–1154 (1989), Hubbard et al. J. Clin. Invest. 84:1349–1354 (1989), Hubbard, et al. Lung Suppl. 565–578 (1990).

Despite the improvements in α1AT augmentation therapy, problems still remain. In particular, previously reported liquid aerosol methods provide effective levels of α1AT in the lung tissue for only short periods, e.g., on the order of several hours, thereby requiring often repeated treatments at higher dosage levels, e.g., >200 mg/day. Thus, there is need for a method of administering α1AT to patients which will provide longer term benefits from a single treatment, thereby requiring lower and fewer doses. The present invention meets these and other needs.

SUMMARY OF THE INVENTION

It is a general object of the present invention to provide methods for pulmonary administration of α1AT dry powder compositions. The methods of the present invention generally provide enhanced persistence of α1-antitrypsin in critical tissues of the lower respiratory tract over previously described administration methods.

The methods of the invention generally comprise providing the α1-antitrypsin as a dry powder. The dry powder α1-antitrypsin is aerosolized and administered pulmonarily to the patient. The methods of the invention are generally useful in treatment of individuals who suffer from a deficiency of α1-antitrypsin, whether genetic or acquired, and are particularly useful in the treatment of the functional derangements of emphysema.

Aerosolization of the dry powder α1AT for pulmonary administration is generally carried out by the use of a dry powder inhalation device. thus, the present invention also provides an apparatus for carrying out the pulmonary administration of α1-antitrypsin dry powders, which device generally includes a housing having a chamber disposed therein, which chamber contains an effective amount of an α1-antitrypsin dry powder composition. The device further includes a gas pressure source fluidly connected to the chamber, for delivering a gas stream to the chamber to aerosolize the dry powder composition. Also included in the device is a delivery system for delivering the aerosolized dry powder composition for inhalation by the patient, fluidly connected to the chamber.

DETAILED DESCRIPTION OF THE INVENTION

I. General

Figure 1:
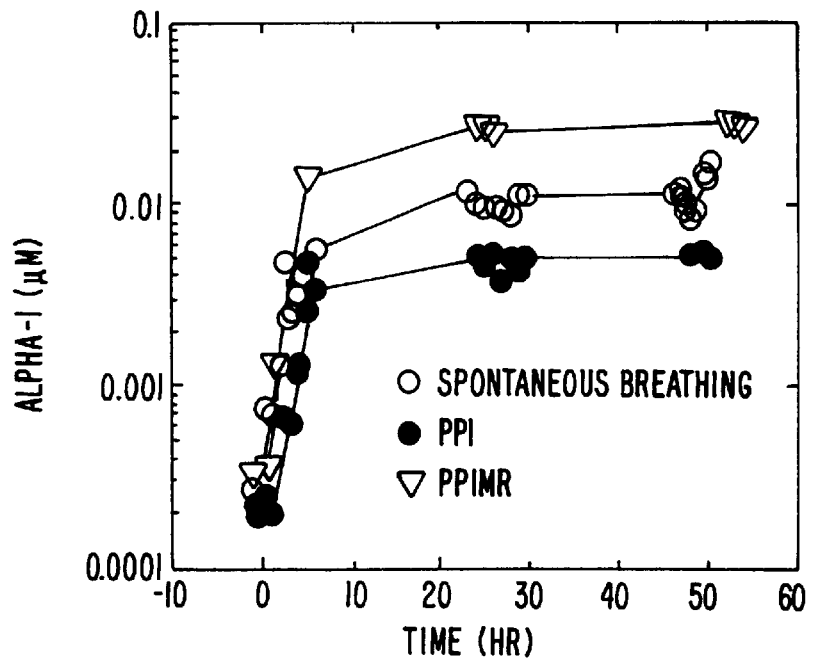
FIG. 1 shows the concentration of α1-antitrypsin in lymph tissue over time, following dry powder aerosol exposure. Three sheep were tested by different exposure protocols.
Figure 2:
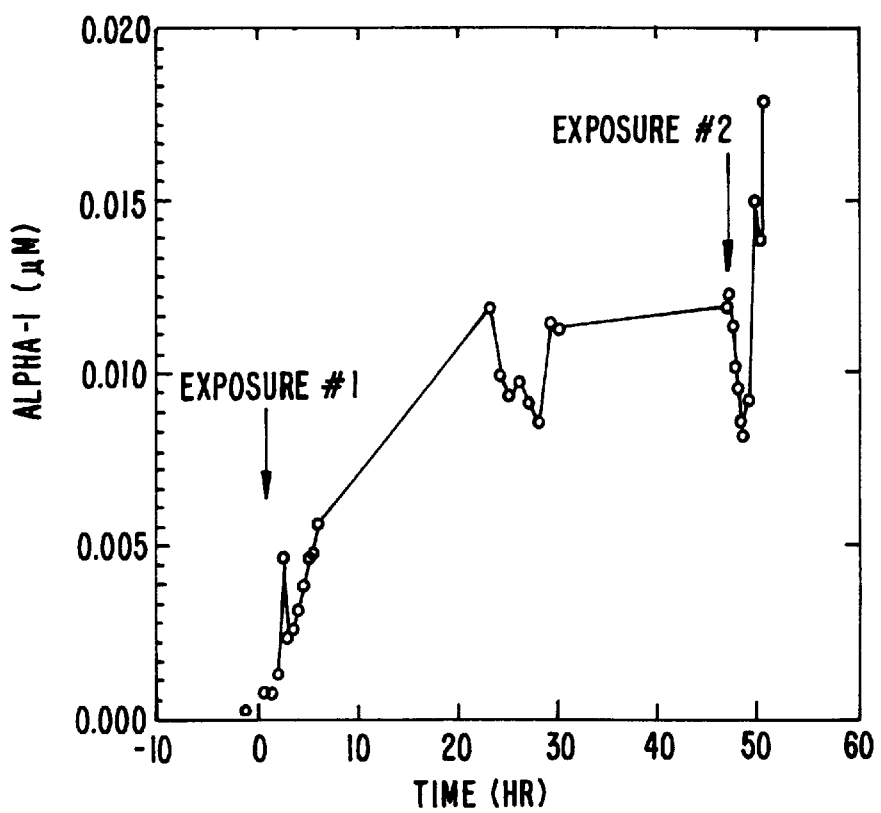
FIG. 2 shows the concentration of α1-antitrypsin in lymph tissue over time, following dry powder aerosol exposure. Two exposures were conducted at time 0 and at 50 hours.

The present invention generally provides methods and apparatuses for administering α1-antitrypsin to a patient. Typically, such administration is useful in treating patients who suffer from a deficiency of endogenous α1-antitrypsin. By "deficiency of endogenous α1AT" is meant that the endogenous levels of α1AT are insufficient to provide protection against the levels of neutrophil elastase that are present. These deficiencies may be manifested as below normal levels of α1AT or as excessive levels of neutrophil elastase in the targeted tissue. The methods of the present invention generally comprise administering α1-antitrypsin dry powder, pulmonarily to the patient. The administration methods of the present invention generally provide enhanced persistence of α1-antitrypsin within the lung tissue over previously described aerosol administration methods.

II. Dry Powder Formulation

Aerosol administration of pharmaceutical compositions has been previously reported in treating a number of disorders. For example, respiratory delivery of aerosolized insulin solutions has been described in substantial detail. See, e.g., Laube, et al., J. Am. Med. Assoc. 269:2106–2109 (1993), Elliott et al., Aust. Pediat. J. 23:293–297 (1987), Wiglet et al., Diabetes 20:552–556 (1971), Corthorpe et al., Pharm. Res. 9:764–768 (1992).

Pulmonary administration of dry powder medicaments, such as insulin, in a large particle carrier vehicle is described in U.S. Pat. No. 5,254,330. A metered dose inhaler for delivering crystalline insulin suspended in a propellant is described in Lee, et al., J. Pharm. Sci. 65:567–572 (1976).

Pulmonary administration of dry powder α1AT may generally be carried out by dry powder administration methods that are known in the art. For example, dry powder administration methods that are particularly suited for the administration and treatment methods of the present invention are described in U.S. patent application Ser. No. 08/423,515, filed Apr. 14, 1995, and incorporated herein by reference in its entirety for all purposes.

α1-antitrypsin ("α1AT") for use in the methods of the present invention may generally be obtained from a variety of sources. For example, both natural and recombinant forms of α1AT are commercially available from, e.g., Cutter Laboratories, Berkeley Calif., and Cooper Labs, Mountain View Calif., respectively. Alternatively, α1AT may be isolated from human sources, e.g., derived from Cohn fraction IV-I of human plasma, or produced by well known recombinant methods. See, U.S. Pat. No. 4,599,311.

Preparation of the dry powder α1AT formulations may generally be carried out using a variety of well known methods including lyophilization, spray drying, agglomeration, spray coating, extrusion processes and combinations of these. In preferred embodiments, the dry powder α1AT formulation is prepared using a spray drying/agglomeration process which produces a substantially amorphous powder of homogenous constitution having a particle size that is readily respirable, has a low moisture content and has flow characteristics that allow for ready aerosolization.

Methods of preparing spray dried, respirable powder compositions are described in, e.g., U.S. application Ser. No. 08/423,515, filed Apr. 14, 1995, and previously incorporated herein. Typically, in the spray drying process, a homogenous aqueous solution of α1AT, which may or may not include a suitable carrier, is introduced via a nozzle, spinning disk or equivalent device into a hot gas stream to atomize the solution to form fine droplets. Although described as a solution, the aqueous form of the α1AT may be in solution, suspension, slurry or other homogenous liquid form, but is preferably in solution. The solvent in which the α1AT is dissolved, suspended or slurried rapidly evaporates from the droplets producing a fine dry powder having particles primarily from 1 to 5 μm in diameter. Preferably, the particle size of the resulting powder is such that more than about 98% of the mass of the dry powder is in particles having a diameter of about 10 μm or less, with more than about 90% of the mass being in particles having a diameter of less than about 5 μm. Alternatively, about 95% of the mass will have particles of less than about 10 μm with about 80% of the mass being in particles having a diameter of less than or equal to about 5 μm.

Spray drying may be carried out using conventional, commercially available spray drying equipment such as that which is available from Buchi, Niro, Yamato Chemical Co., Okawara Kakoki Co. and the like, which equipment is generally capable of producing an amorphous powder product. Typically, these machines are capable of operating across a wide range of parameters. For example, a Buchi-190 spray dryer may be utilized to prepare the dry powder compositions by operating at between 5 and 20 ml/min, with an atomizing pressure of 50 to 120 psi, an atomizing air feed rate of 20 to 80 lpm and a drying temperature of from 50 to 200° C.

For the spray drying process, such spraying methods as rotary atomization, pressure atomization and two-fluid atomization can be used. Examples of the devices used in these processes include the Parubisu Mini-Spray GA-32 and "Parubisu Spray Drier DL-41," manufactured by the Yamato Chemical Co., or the CL-8, L-8 FL-12, FL-16 or FL-20 model spray driers manufactured by Okawara Kakoki Co. This equipment can be readily employed for spray drying the compositions described herein, including rotary disk atomizer spray drying methods.

The above described dry powders are readily useable in the methods described herein. However, in some aspects, it may be desirable to provide the dry powder formulation in a form that possesses better handling characteristics, e.g., flowability, low caking and the like. Production of aggregate or agglomerate compositions is described in, e.g., U.S. application Ser. No. 08/483,467, filed Jun. 7, 1995, and incorporated herein by reference in its entirety for all purposes. In a particular aspect, the dry powder formulations described herein are provided as aggregates or agglomerates of the above described fine powder compositions.

Generally, agglomeration of the above described fine powder compositions is carried out by combining the powder of fine particles with a binding liquid to produce a wetted mass. The wetted mass is then divided into small volumes which are dried to remove the binding liquid and to produce dry powder agglomerate units having a first size distribution. This is typically carried out by well known methods, e.g., extrusion. Extrusion methods typically involve the extrusion of the wetted mass or paste through a screen having holes that are in the range of 40–650 μm and more preferably in the range of from about 150–500 μm. The holes in the screen are typically circular in geometry, thereby producing an elongated cylindrical extrudate. The extrudate is typically dried at a temperature of from about 15° C. to about 40° C., depending upon the nature of the material being dried. Typically, forced air convection driers or vacuum driers are used in drying the extrudate. Typically, vacuum dryers will subject the aggregate particles to a pressure of from about 250 to about 650 mm Hg.

Binding liquids may include a variety of liquids compatible with the pharmaceutical compositions being prepared, e.g., water, saline, and the like. Additionally, in some aspects, the binding liquid is a nonaqueous solvent, e.g., fluorocarbon, toluene, xylene, benzene, acetone, hexane, octane, chloroform and methylene chloride. The use of nonaqueous solvents as binding liquids is generally advantageous as carbohydrates and proteins that are generally included in the agglomerate compositions described herein typically have low solubility in these liquids, thereby minimizing the potential for formation of crystalline bridges between the fine powder particles in the agglomerate. Further, most nonaqueous solvents have a low surface tension allowing the larger agglomerate particles to be broken down when needed.

Examples of preferred nonaqueous solvents include fluorocarbon liquids such as perfluorodecalin and perfluorooctyl bromide. Fluorocarbon liquids are typically preferred due to their hydrophobic and lipophobic nature that does not dissolve or otherwise interact with proteins or carbohydrates. The high vapor pressure of fluorocarbon liquids is also useful in removing the liquid from the agglomerate particle. These fluorocarbon liquids are also generally biocompatible in most pharmaceutical compositions, and are generally commercially available from a variety of commercial suppliers, e.g., PCR, Inc. (Gainesville, Fla.), Sigma Chemical Co. (St Louis, Mo.) and Aldrich Chemical Co. (Milwaukee, Wis.).

The amount of binding liquid added to the dry powder composition is generally based on the surface area of the fine particles. For example, where a fluorocarbon binding liquid is used with the fine particles of the initial dry powder compositions, e.g., those having a size range of from 1–5 $\mu$m, the liquid is added to the powder in the range of from about 0.5 gram to 5 grams liquid per gram of powder.

The dry powder agglomerates produced in this first series of steps are then adjusted to have a second size distribution characterized by a friability index of from about 10 to about 60. When adjusted, the aggregate particles will typically be durable enough to resist breaking apart during normal handling and metering procedures. At the same time, the particles are typically sufficiently friable to allow the aggregates to be broken up when needed, i.e., during administration. Friability indices are generally calculated by placing a small sample, e.g., 0.4 to 0.5 g, of the aggregate composition on a 1000 $\mu$m screen. The screen is vibrated at an amplitude of approximately 1 cm and a frequency of approximately 5 Hz for 20 minutes. After 20 minutes, the aggregates remaining on the 1000 $\mu$m screen are weighed and this weight is then divided by the beginning weight. The percentage of aggregates that have not broken down through the 1000 $\mu$m screen is the friability index.

Adjustment of the aggregate particle composition to the second size distribution is generally carried out by sieving the agglomerate composition through a series of screens or sieves having a desired screen size range. For example, where a size range distribution of from about 150–500 $\mu$m is desired, the aggregated particles are placed on a set of stacked screens. The top screen will have a passage of approximately 500 $\mu$m, whereas the bottom screen will have a passage of 150 $\mu$m. The aggregate particles are placed on the top screen and sieved, i.e., by vibration and/or tapping. All particles exceeding the 500 $\mu$m size limit are retained on the top screen from which they may be discarded or subjected to reprocessing. Particles smaller than 500 $\mu$m will pass to the bottom screen where particles exceeding 150 $\mu$m will be retained. Those particles that pass the second screen are collected, i.e., in a pan below the second screen, from which they may be discarded or reprocessed.

Typically, the second size distribution will have a mean particle size between about 50 $\mu$m and about 600 $\mu$m, preferably between about 150 $\mu$m to about 500 $\mu$m, and most preferably between about 200 $\mu$m and 500 $\mu$m. The agglomerates are typically formed/selected whereby greater than 90% of the agglomerate composition falls within a size range that is ±250 $\mu$m, and preferably within a range of ±150 and more preferably within about ±100 $\mu$m.

The dry powder agglomerates may also be spheronized, i.e., given a spherical geometry, by well know methods, e.g., rolling methods, such as those commonly used in pan coating operations. This typically involves rolling the particles in a container to result in a spherical particle being produced.

Agglomerate compositions may also be prepared in fluid bed drying apparatuses. Typically, this involves first fluidizing the dry powder composition in a stream of hot air. The binding liquid is then sprayed into the fluidized powder through a nozzle. The wetting of individual particles allows for the agglomeration of other particles thereto. The concurrent drying of the hot air stream prevents formation of agglomerates having low friability. Fluid bed dryers are also commercially available from, e.g., Glatt Air Techniques, Inc.

Dry powder compositions may also be prepared using other drying processes such as agglomeration processes, extrusion, spray coating and lyophilization and jet milling processes. Lyophilization/jet milling processes for preparation of dry powder polypeptide formulations are described in, e.g., Published PCT Application No. WO 91/16038.

In preferred aspects, the dry powder $\alpha$1AT compositions for use in the methods described herein will be substantially pure. By substantially pure, is meant that within the dry powder formulation, $\alpha$1AT will make up the predominant component on a weight/weight basis. Typically for example, the dry powder formulation will be greater than about 30% $\alpha$1AT by weight. In preferred aspects, the dry powder formulation will be greater than about 70% $\alpha$1AT by weight, more preferably greater than about 80% $\alpha$1AT by weight. In still more preferred aspects, the dry powder formulation will be greater than about 90% $\alpha$1AT by weight with dry powder formulations of greater than about 95% $\alpha$1AT and greater than about 99% being most preferred. Calculation of weight percent of $\alpha$1AT may be carried out by any of a variety of well known methods, e.g., immunosorbent assays, activity based assays, and the like.

Where the dry powder composition contains elements other than $\alpha$1AT, the remaining fraction of the composition may generally comprise one or more of a number of other elements. For example, the dry powder composition may contain products of the spray drying process, i.e., inactive $\alpha$1AT species, or other macromolecular components remaining from the preparation of the $\alpha$1AT. In particularly preferred aspects, however, pure or nearly pure $\alpha$1AT is used to formulate the dry powder compositions. In particular, $\alpha$1AT compositions that are greater than 90% and more preferably greater than 95% pure, are used to formulate the dry powder compositions.

In addition to the above described additional elements, a variety of adjuncts may be added to the dry powder formulation, either during the spray drying process or after the spray drying process by addition of a dry component via dry powder blending methods. For example, in some aspects, it may be desirable to combine the $\alpha$1AT with one or more pharmaceutical carriers or excipients which are suitable for respiratory and pulmonary administration. Such carriers may serve as bulking agents, e.g., when it is desirable to reduce the concentration of the $\alpha$1AT delivered to the patient in a single dose, or may serve to enhance the efficacy of the formulation, either as a stabilizing agent for the dry powder composition, a dispersing agent to enhance the handling properties of the formulation, an adjuvant that enhances the activity of the $\alpha$1AT within the tissue of the lung, e.g., buffering agents and the like. Examples of suitable pharmaceutically acceptable excipients or bulking agents include carbohydrates, polypeptides, amino acids or combinations thereof. Suitable carbohydrates include, e.g., monosaccharides such as galactose, D-mannose, sorbose and the like, disaccharides, such as lactose, trehalose and the like, cyclodextrins, such as 2-hydroxypropyl-$\beta$-cyclodextrin, and polysaccharides, such as raffinose, maltodextrins, dextrans and the like, alditols, such as mannitol, xylitol and the like. Preferred carbohydrates include lactose, trehalose, raffinose, maltodextrins, and mannitol. Suitable polypeptides include, e.g., aspartame and the like, whereas suitable amino acids include, e.g., alanine and glycine.

The carrier materials may be combined with the α1AT prior to spray drying, e.g., by adding the carrier to the α1AT solution. This ensures that the carrier is dried simultaneously with the α1AT to produce a homogenous dry powder. Alternatively, the carriers may be separately dried or obtained as a dry powder, and blended with the α1AT powder. Dry powder carriers for blending with α1AT dry powders are typically crystalline (to reduce water absorption) but may also be amorphous. The size of the carrier may generally be selected to improve the flowability of the α1AT powder, typically in the range of from about from about 25 $\mu$m to about 100 $\mu$m. Crystalline lactose is a particularly preferred dry powder carrier.

While it is possible to administer the α1AT ingredient in pure form, i.e., without adjunct ingredients, it is often desirable to include additional components with the α1AT, e.g., provide the α1AT as part of a pharmaceutical formulation. These formulations comprise the α1AT in a therapeutically or pharmaceutically effective dose together with one or more pharmaceutically or therapeutically acceptable carriers and optionally other therapeutic ingredients. Various considerations are described, e.g., in Gilman et al. (eds) (1990) Goodman and Gilman's: The Pharmacological Bases of Therapeutics, 8th Ed., Pergamon Press; Novel Drug Delivery Systems, 2nd Ed., Norris (ed.) Marcel Dekker Inc. (1989), and Remington's Pharmaceutical Sciences, 18th Ed. (Mack Publishing Co. 1990), the full disclosures of which are incorporated herein by reference. Specific examples of adjunct components in the α1AT formulations described herein include, e.g., bulking agents, buffers, and other pharmaceutical agents for co-administration with the α1AT, such as carbohydrate carriers and the like.

III. Administration

In a particular aspect, the present invention provides a method of pulmonarily administering α1AT dry powder to a patient. Such methods are particularly useful in the treatment of patients suffering from disorders characterized by a deficiency of α1AT within the tissues of the lung. These disorders may be a result of a genetic deficiency or a consequence of external influences, e.g., chronic smoking, etc. By administering α1AT pulmonarily, as a dry powder composition, an enhanced persistence of α1AT in the tissues of the lung is obtained.

By "pulmonary administration" or "administering pulmonarily" is meant a route of administration that delivers an effective amount of the compound so administered to the tissues of the lower respiratory tract. Such administration generally entails inhalation of the subject compound by the patient, thereby drawing the compound into the deep lung.

Delivery of powdered medicaments to the lungs is typically accomplished by use of an inhalation device which fluidizes the powdered medicament in an airstream which can then be inhaled by the patient to deliver the medicament to the patient's lungs. By providing the aggregated particles having a desired friability index, as described previously, the aggregated particles can be broken down into powdered form within the inhaler. In this way, the powdered medicaments can remain in agglomerate form for measurement and handling until needed for pulmonary delivery by the inhaler.

The aggregated particles are generally delivered to the inhaler in unit dosage receptacles, commonly referred to as blister packs or cartridges. The manufacture of blister packs is typically carried out by methods that are generally well known in the packaging art. To extract the aggregated particles from the receptacle, a wall of the receptacle is pierced when the receptacle is inserted into the inhaler, or while within the inhaler. With the receptacle opened, the aggregated particles are extracted into a gas stream that has sufficient disruptive force, i.e., shear force, to break down the aggregated particles into their constituent fine powder elements. Typically, adequate disruptive forces are supplied by a gas stream having a sonic velocity. In alternative aspects, the blister pack or receptacle may be subjected to vibratory energy prior to piercing of the receptacle to break down the aggregate particles into the substituent fine powder.

Typically, the aggregate particles will be substantially broken down to their substituent fine powder elements prior to inhalation. For example, typically greater than 30% of the aggregate particles subjected to the disruptive forces of the gas stream will be broken down. Preferably, at least about 50% of the aggregate particles will be broken down and most preferably, greater than about 70% of the aggregate particles will be broken down when subjected to the gas stream, etc. prior to inhalation by the patient. By "broken down" is meant disintegration of the larger aggregate particles, as described above to the smaller fine powder particles, also described above, e.g., the fine powder particles having a diameter of from about 1 $\mu$m to about 5 $\mu$m.

When the aggregate particles are within the desired size range of 200–50 $\mu$m, substantially complete removal of the aggregate particles from the receptacle is obtainable, as larger sized aggregates may become trapped behind the pierced walls of the receptacle. By "substantially complete removal" is meant greater than about 55%, preferably, greater than about 70%, and more preferably, greater than about 90% by weight.

A variety of inhalation devices have been previously described for aerosol administration. See, e.g., U.S. Pat. Nos. 4,137,914, 4,174,712, 4,524,769, 4,667,688, and Published PCT Application Nos. PCT/SE93/00389, PCT/SE93/01053, PCT/DK90/00005 and U.S. patent application Ser. No. 08/309,691, filed Sep. 21, 1994. A particularly preferred dry powder inhaler is that described in U.S. patent application Ser. No. 08/487,184. Generally, this inhaler device is particularly suited for the delivery of dry powder compositions that are formed from discrete fine powder particles ranging in size from 1–5 $\mu$m. The preferred device generally employs a two-step dispersion technique to achieve optimal dispersion of the dry powder composition. Typically, the powder composition, e.g., the aggregate or agglomerate composition, is fluidized within a unit dosage receptacle, such as a blister pack. The fluidized agglomerate particles are then dispersed in the high velocity gas stream under conditions which break up such agglomerated particles into their constituent powder elements. Such complete dispersion can be achieved with very low volumes of high velocity air and having relatively high particle concentrations. This apparatus is also capable of use with compositions containing greater amounts of diluents, e.g., bulking agents, and the like.

The device generally incorporates a feed tube having a powder inlet end which is inserted into the receptacle, i.e. through a penetration in the lid or access surface of the receptacle. A high velocity airstream is flowed past the outlet end of the feed tube, drawing the powder from the receptacle into the airstream to form the desired aerosol. The velocity of the airstream, as described above, is typically sonic, to allow for break-up of agglomerate particles. Typically, a second penetration is also provided in the receptacle to allow a separate stream of fluidization air to enter the receptacle and sweep the aerosolized powder, ensuring maximal recovery of the powder from the receptacle.

The high pressure gas stream is typically generated by abruptly releasing a charge of pressurized gas through a flow path that intersects with the outlet end of the feed tube at an angle selected to both (1) induce sufficient fluidization air flow through the feed tube to fluidize and transport the powder in the receptacle and (2) break up powder agglomerates which remain as the powder exits from the outlet end of the feed tube. The gas pressure prior to release will usually be at least about 15 psig (to achieve sonic velocity), preferably being at least 20 psig, and usually being in the range from 40 to 80 psig. The expanded volume of gas (measured at standard temperature and pressure ("STP") of 14.7 psig and 20° C.) will therefore usually be in the range of from 2 ml to 25 ml, and preferably 4 ml to 15 ml. The release of the high pressure gas can be effected by a manual trigger or optionally by sensing negative pressure caused by a patient's inhalation (i.e., breath activated).

The aerosolized powder will also typically be captured within a plume capture chamber, prior to inhalation by the patient, to avoid difficulties associated with delivering a high pressure dose directly to the patient. The aerosolized powder within the plume chamber is then inhaled by the patient concurrently with, and/or followed by breathing ambient air, i.e., through a separate inlet in the plume chamber, which aids in sweeping the entire dose of the powder from the plume chamber and forcing the powder into the deep lung.

IV. Therapeutic Applications

The methods of the present invention are particularly applicable in therapeutic applications for the treatment of patients who are deficient in, or could otherwise benefit from augmentation of increased levels of α1AT in the tissues of the lung. As described above, examples of such patients include genetic disorders characterized by low plasma and lung levels of the α1AT inhibitor and the functional derangements of pulmonary emphysema.

By "patient" is generally meant a mammalian patient for whom treatment is sought. Although the methods described herein may be generally applicable to a variety of mammalian species, preferably, as used herein, the term patient will generally refer to human patients.

By "treatment of a patient" is meant the full spectrum of therapeutic treatments for a particular disorder ranging from a partial alleviation of symptoms to an outright cure for the particular disorder. Treatment is typically effected by the pulmonary administration of a therapeutically effective amount of dry powder α1AT. By "therapeutically effective amount" is meant an amount of α1AT that is sufficient to effect treatment of the particular disorder for which treatment is sought, i.e., sufficient augmentation of α1AT levels in the lower respiratory tract. Typically, such therapeutically effective amounts will be sufficient to provide an amount of α1AT within the tissue of the lower respiratory tract that is similar to that of non-deficient individuals.

Typically, treatment of the above described disorders will be affected by administering dosages of α1AT dry powder that total in the range of from about 1 to about 80 mg of α1-antitrypsin daily. Preferably, a therapeutically effective amount will range from about 5 to about 25 mg of α1-antitrypsin daily, and more preferably, from about 10 to about 20 mg of α1-antitrypsin daily. In particularly preferred aspects, the methods of the present invention and as described above, may be used in the treatment of patients suffering from pulmonary emphysema. To achieve the desired therapeutic amount, it may be desirable to provide for repeated administrations, i.e., repeated individual inhalations of a metered dose. The individual administrations are repeated until the desired daily dose is achieved.

As described above, the methods of administering the dry powder α1AT to the patient generally include providing α1AT as a dry powder, aerosolizing that powder, and presenting it to a patient for inhalation. This is generally carried out using the methods and apparatuses that are substantially described above.

The present invention is further illustrated by the following examples. These examples are merely to illustrate aspects of the present invention and are not intended as limitations of this invention.

V. Examples

Example 1—Spray Drying of α1AT

Purified human plasma α1AT was supplied by Armour Pharmaceutical Co., Kankakee, Ill. The α1AT was formulated in citrate buffer. The buffered α1AT was spray dried into a fine dry powder composition. Spray drying was carried out using a Buchi-190 spray dryer with a feed rate of 5 ml/min, an atomization pressure of 120 psi, an atomizing feed rate of 80 lpm and a drying temperature of 80° C. The majority of the mass of the composition had a respirable particle size (aerodynamic diameter less than 5 μm). The dry powder composition contained approximately 73% α1AT, 3.7% moisture and 16.9% bulking agent. The specific inhibitory activity of the powder was determined by assaying the inhibitory activity of the powder against trypsin. The powder assayed at approximately the same specific activity as the protein prior to drying.

Blister packages were filled with 5 mg of the powder composition under controlled conditions and were stored in desiccated pouches at room temperature until used. Stability analysis of α1AT in the dry powder aerosol over time of the experiments confirmed that there was no detectable loss of activity as measured by the trypsin inhibition assay.

Physical stability of α1AT dry powder was characterized by the following parameters: (1) Mass median aerodynamic diameter (MMAD), as determined by a California Instrument cascade impactor operated at 12.5 lpm; (2) respirable fraction (mass having an aerodynamic particle size less than 5 μm); and (3) dispersibility as measured by filter collection at the mouthpiece of the aerosolization device at 30 lpm for 2.5 seconds (see Table I).

TABLE I

| Time | Dispersibility (STD) | MMAD | Resp. Fract. % < 5 μm |
|---|---|---|---|
| Initial | 63.6 (3.5) | 1.3 | 90 |
| Pre-study (3 mos.) | 72.6 (9.3) | 1.3 | 90 |
| Post-study (6 mos.) | 72.5 (6.3) | 1.2 | 92 |

Example 2—Evaluation of Aerosol Exposure of α1AT in Sheep Models

Mixed breed sheep (36±3 kg) were used to determine optimal administration methods for the dry powder α1AT composition. One sheep was studied at a time. Two days prior to aerosol exposure, the caudal efferent lymphatic duct, carotid artery and jugular vein of the sheep were cannulated under general anesthesia (lymph duct cannula: 030×050 Tygon tubing, Fisher Scientific Co., artery and vein cannula: Extension tube, Baxter-Pharmaceal, CAT No. K751L). On the day of exposure, the sheep to be studied was anesthetized with 500 mg pentothal administered intravenously (thiopental sodium, Abbott Labs, IL) and intubated with a size 10 ID endotracheal tube.

Three different exposure techniques were examined (See, Table II), two positive pressure ventilation techniques and one spontaneous breathing technique. In the positive pressure inhalation models, two ventilation modes were evaluated in two separate sheep (sheep #1 and #3). Sheep #1 was ventilated 15 breaths/minute at 400 ml/breath with breathing-quality oxygen containing 1% Halothane (Halocarbon, NJ) using a Harvard ventilator piped through a dry powder inhalation device. Sheep #3 was injected with 60 mg i.v. succinylcholine, a muscle relaxant, and was ventilated 10 breaths/minute at 600 ml/breath with oxygen containing 1% Halothane. In the spontaneous breathing model, Sheep #2 was injected with Ketamine to provide anesthesia, 25 mg/kg i.v. (Ketaset, Fort Dodge Lab, Inc. Iowa), and was allowed to breath ambient air through the dry powder inhalation device. Aerodynamic size distribution was measured using the California Measurements cascade impactor. The aerosol mass median aerodynamic diameter and the respirable fraction (mass fraction having less than 5 $\mu$m aerodynamic particle size) were 1.3±0.1 $\mu$m and 90%, respectively. This formulation had a dispersibility of 63±3% in the device used.

Evaluation of the three exposure techniques involved measurement of (1) the portion of aerosol available for inhalation (% of aerosol available at the mouthpiece of the inhalation device) and (2) lymph and plasma levels of $\alpha$1AT.

Evaluation of the device efficiency, e.g., the ability to deliver aerosol to the endotracheal tube, was measured to be 23±1%, 32±4% and 31±1%, for the positive pressure inhalation model without the muscle relaxant ("PPI") (15 breaths/minute, 400 ml/breath) the positive pressure with muscle relaxant ("PPIMR") (10 breath/minute, 600 ml/breath) and the spontaneous breathing model (100–200 ml/breath), respectively.

Prior to exposure, lymph and blood were sampled to establish background levels of $\alpha$1AT. Each animal was exposed to 100 mg of packaged $\alpha$1AT dry powder aerosol. Lymph and blood samples were taken every 30–60 minutes for 6 hours and then at 24–26 and 48–50 hours, post dosing. Sheep #2, the spontaneous breathing animal was exposed again to aerosol $\alpha$1AT at 50 hours after the first exposure and was lavaged 5 hours later.

At the end of each study, blood was drained while the lungs were kept ventilated to prevent them from collapsing, then each lung was completely lavaged. This was carried out by surgically exposing the neck and chest, and lavaging one lung at a time by clipping the other lung shut and injecting 6×200 ml isotonic saline washes through a Tygon tube connected to a 50 ml syringe. The recovered washes from each lung were pooled together to give a total lung lavage sample. All samples, lymph and blood, were placed on ice until they were centrifuged for 3 minutes at 3000 rpm. They were kept frozen at –70° C. until they were analyzed by ELISA.

Table II shows the efficiency of the devices used for the aerosol delivery of the $\alpha$1AT to the entrance of the endotracheal tube (shown as Respirable %) for the various delivery methods. Also shown is the peak lymph level of $\alpha$1AT.

TABLE II

| Sheep # | Inhalation Model | Respirable % | Peak Lymph Level of $\alpha$1AT (nM) |
|---|---|---|---|
| 1 | Positive pressure: 15 breaths/minute; 400 ml/breath | 23 ± 1 | 5.8 |
| 2 | Spontaneous breathing: 100–200 ml/breath | 32 ± 4 | 12.2 |
| 3 | Positive Pressure: 10 breaths/minute; 600 ml/breath; paralyzed animal | 31 ± 1 | 29.4 |

$\alpha$1AT dry powder aerosol administered pulmonarily to sheep, as described above, increased the levels of $\alpha$1AT in the lymph from 0.3 nM (0.014 $\mu$g/ml) to 5.8 nM (0.29 $\mu$g/ml), 12.2 nM (0.61 $\mu$g/ml) and 29.4 nM (1.47 $\mu$g/ml) and increased blood $\alpha$1AT levels from 0.6 nM (0.03 $\mu$g/ml) to 1.9 nM (0.093 $\mu$g/ml), 4.3 nM (0.217 $\mu$g/ml) and 7.6 nM (0.38 $\mu$g/ml) at 48 hours post exposure in Sheep #1, 2 and 3, respectively. See FIG. 1.

In sheep #2, which was initially exposed to $\alpha$1AT aerosol by the spontaneous breathing method, described above, and again after 50 hours by positive pressure inhalation (600 ml/breath, without relaxant), the lymph level of $\alpha$1AT after the second exposure rose from 0.61 $\mu$g/ml to 0.92 $\mu$g/ml within 5 hours after the second exposure.

$\alpha$1At levels in the epithelial lining fluid ("ELF") were 0.4 $\mu$M in Sheep #1 (lavaged 50 hours post exposure) and 1.3 $\mu$M in sheep #3 (lavaged 72 hours post exposure). In sheep #2, which was exposed a second time at 50 hours after the initial exposure, $\alpha$1AT levels in the ELF were 2.9 $\mu$M (lavaged 5 hours after the second exposure). These values were calculated from the lavage washes assuming 20 ml of ELF.

The PPMR technique used in Sheep #3 gave the highest lymph levels of $\alpha$1AT and was selected for use in subsequent examples.

Example 3—Determination of Deposited Dose in Sheep

Three sheep were pulmonarily administered $\alpha$1AT dry powder according to the PPIMR method described above. The lungs were lavaged immediately following aerosol administration. The average deposited dose was calculated by multiplying the concentration of $\alpha$1AT in the lavage by the lavage volume. The average deposited dose was calculated at 7.2±3.1 mg. This translated to a deposition efficiency of approximately 8% for this sheep exposure system. The data for each sheep is shown in Table III, below.

TABLE III

| Sheep # | Recov'd Lavage (ml) | | $\alpha$1AT in Lavage ($\mu$g/ml) | | Deposited Dose |
|---|---|---|---|---|---|
| | Right | Left | Right | Left | |
| 5 | 850 | 825 | 1.53 | 12.8 | 10.6 |
| 8 | 950 | 930 | 0.10 | 4.83 | 4.6 |
| 9 | 925 | 950 | 2.80 | 3.85 | 6.3 |
| | | | | Average ± STD | 7.2 ± 3.1 |

Figure 3:
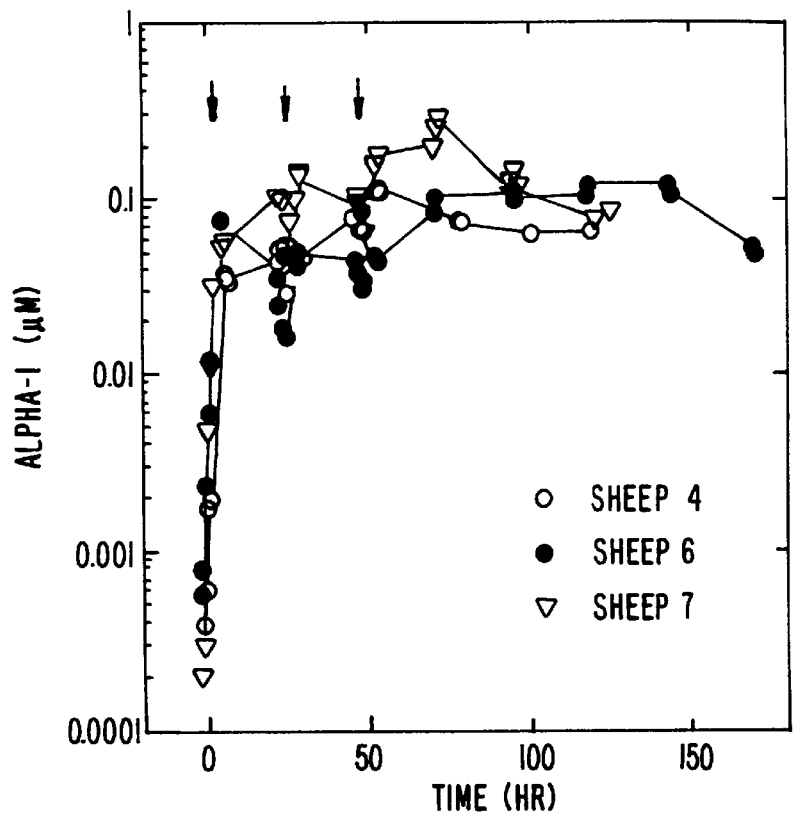
FIG. 3 shows α1AT levels recovered from sheep pulmonary lymph following multiple administrations by inhalation. Aerosol administrations are marked by arrows.
Figure 4:
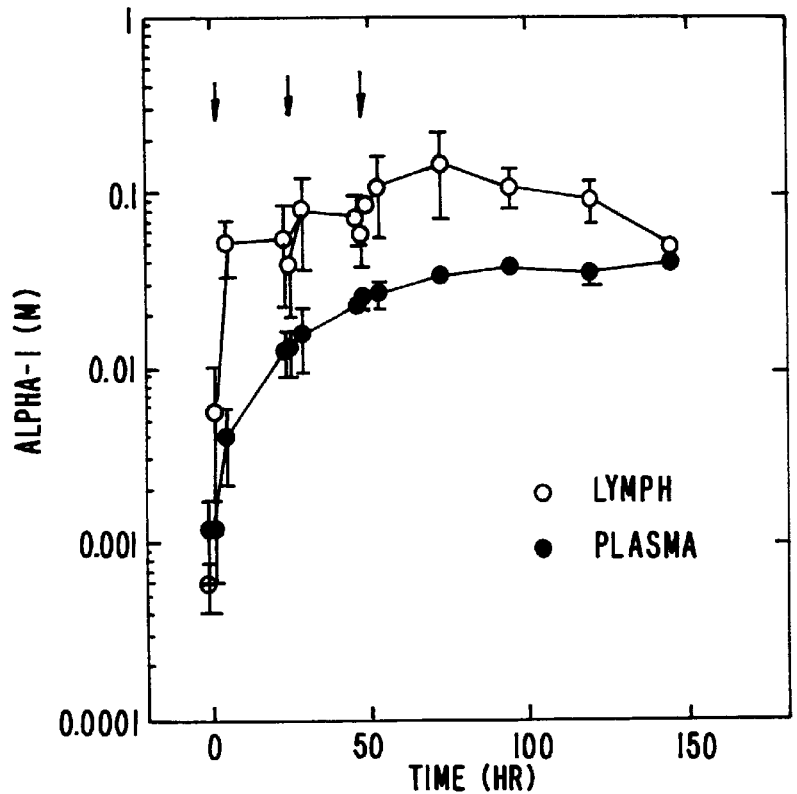
FIG. 4 shows mean lymph and plasma concentrations of α1AT in sheep (n=3) following multiple administrations. Administrations are marked by arrows.

Pulmonary absorption of pulmonarily administered dry powder $\alpha$1AT was tested using the PPIMR technique described above. Again, three sheep were administered α1AT dry powder aerosol in three doses each, at time 0, at 24 hours and at 48 hours. Levels of α1AT were measured in the lymph, plasma and in the 'end-of-study' epithelial lining fluid (ELF).

α1AT dry powder deposited in sheep lungs increased lymph levels of exogenous α1AT to an average peak level of 142±73 nM (7.4±3.8 μg/ml). FIG. 3 shows the lymph profiles of each of the individual sheep, with the mean profile being shown in FIG. 4 (0). The concentration/time curves exhibited a prolonged absorption profile (FIGS. 3 and 4). The total amount of α1AT cleared by the lymph was calculated by multiplying the area under the curve (AUC) of the concentration profile by the average lymph flow rate (See Table IV).

Levels of exogenous α1AT in plasma were also increased to an average level 36.2 nM (1.9±0.1 μg/ml). The mean plasma levels of α1AT over time are shown in FIG. 4 (•). The amount of α1AT absorbed from the lungs into the circulation is the peak concentration multiplied by the volume of distribution of plasma (steady state volume of distribution of sheep plasma is 109±16 ml/kg body weight as measured by IV injections of radio-labeled α1AT, Smith, et al., J. Clin. Invest. 84:1145–1154 (1989). The amounts of α1AT found in the plasma are also shown in Table IV.

Addition of the contributions of both plasma and lymph levels gives the total recovery of 12.0±2.9 mg which equals 55±13% of the deposited dose (See, Table 4).

TABLE IV

| Sheep # | AUC | Avg. Lymph Flow Rate (ml/hr) | Amt (mg) cleared by: | | Total Clearance | Fraction Absorbed (%) |
|---|---|---|---|---|---|---|
| | | | Lymph | Plasma | | |
| 4 | 0.402 | 6.5 ± 2.6 | 2.6 | 6.1 | 8.7 | 40 |
| 6 | 0.712 | 9.2 ± 3.6 | 6.6 | 7.4 | 14.0 | 65 |
| 7 | 0.795 | 7.9 ± 3.2 | 6.3 | 6.6 | 13.2 | 61 |
| Avg. | 0.636 ± 0.207 | 7.8 ± 3.2 | 5.2 ± 2.2 | 6.7 ± 0.6 | 12.0± 2.9 | 55 ± 13 |

Epithelial lining fluid (ELF) volume was measured by Peterson, et al., Am. Rev. Respir. Dis. 141:314–320 (1990) to be 11.4 ml in a 38 kg sheep. To measure ELF levels of α1AT, sheep having an average weight of 29 kg were used. In a 29 kg sheep, the ELF volume was assumed to be approximately 10 ml, or 5 ml/lung. α1AT levels in ELF were determined as the amounts recovered by lavage from each lung, divided by 5 ml. Table V lists the number of aerosol doses, time of lavage after the last dose and the calculated ELF levels of α1AT in each lung. Protective levels of α1AT in ELF (1.7 μM) were easily achieved in all sheep studied in the absorption experiments, even when lavaged 3 days after the final dose. Additionally, the amounts of α1AT recovered in the lavage of the three sheep used in the absorption study (Sheep 4, 6 and 7) were measured at 13.4±7.3 mg or approximately 62% of the deposited dose.

Although the deposition efficiency in these models is somewhat low (8%), this appears to be attributable to the inefficiency of the aerosolization device when it is connected to the ventilator. In particular, losses due to the plumbing leading up to the endotracheal tube and the low inhalation volume using the ventilator account for a large amount of the lost material. Additionally, the build up of mucous around the endotracheal tube results in increased deposition within the plumbing and device as a result of the narrowed windpipe and disturbed air flow patterns.

TABLE V

| Sheep # | No. of Doses | Time of Lavage after final dose (hr) | α1AT Levels in ELF (mg) | | Amts. Recov'd by Lavage (mg) |
|---|---|---|---|---|---|
| | | | Right Lung | Left Lung | |
| 1 | 1 | 52 | 1.5 | 2.7 | 1.1 |
| 2 | 2 | 51 | 10.0 | 9.4 | 5.0 |
| 3 | 1 | 52 | 5.0 | 2.5 | 2.0 |
| 4 | 3 | 72 | 6.1 | 11.8 | 13.2 |
| 6 | 3 | 96 | 24.4 | 55.8 | 20.8 |
| 7 | 3 | 72 | 12.3 | 9.3 | 6.2 |
| 5 | 1 | <1 | 5.4 | 45.8 | 10.6 |
| 8 | 1 | <1 | 0.4 | 17.3 | 4.6 |
| 9 | 1 | <1 | 10.0 | 14.1 | 6.3 |

Example 4—Estimation of Interstitial α1AT

Figure 5:
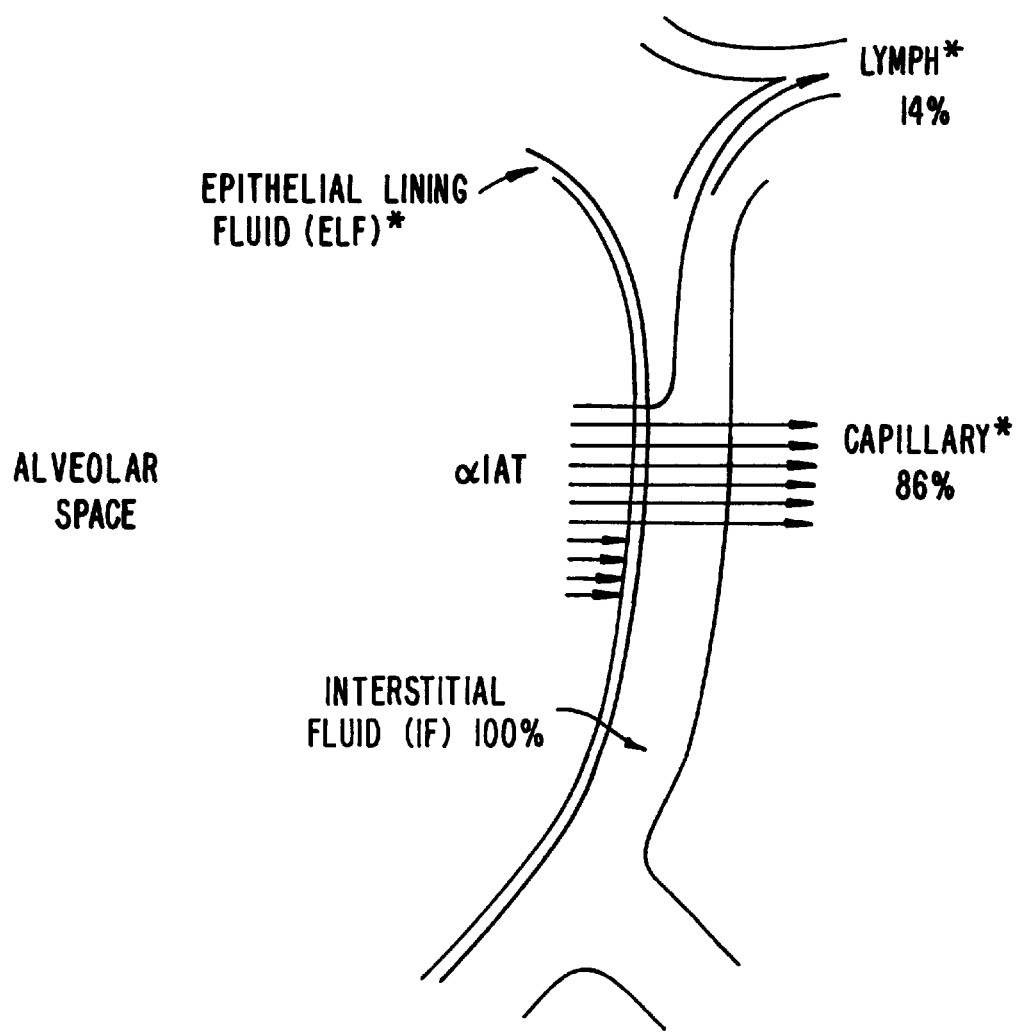
FIG. 5 illustrates a schematic of alveolar structures involved in the movement of α1AT from the alveolar airspace into the plasma.

The above described experiments illustrate that dry powder α1AT administered as an aerosol is absorbed from the alveolar surface into the lung. Once in the interstitium, α1AT may either be absorbed directly into the blood or it may diffuse into the lymphatics (See FIG. 5).

In the above experiments, the majority of inhaled α1AT crosses directly through the interstitium into the blood. The rest was transported into the circulation by lymphatic filtration. Staub et al., J. Surg. Res. 19:315 (1975). In this sheep model, the average amount of α1AT cleared in 24 hours by the lymph following one aerosol administration was approximately ⅙ the amount that was found in the plasma (See Table VI). In a similar sheep model, Smith et al. (J. Clin. Invest 84:1145–1154(1989)) calculated the rate of clearance of α1AT out of the lungs at 16.1±10.4% of the total rate of α1AT transported out of the lung. This is consistent with the instant results (See Table VI). Plasma and lymph levels exhibited a similar profile (See FIG. 4). Thus, it may be assumed that for each α1AT molecule cleared by the lymph, 6 molecules are transported across the endothelial barrier into the bloodstream. Taking the non-lymph clearance into account, the concentration of α1AT in the interstitial fluid should be approximately 7 times that measured in the lymph (See FIG. 5).

TABLE VI

| Sheep # | Lymph (μg) | Plasma (μg) | Plasma/ Lymph |
|---|---|---|---|
| 1 | 32.4 | 239 | 7.4 |
| 2 | 73.2 | 631 | 8.6 |
| 3 | 144.6 | 752 | 5.2 |
| 4 | 278 | 2200 | 7.9 |
| 6 | 757 | 3100 | 4.1 |
| 7 | 489 | 1300 | 2.7 |
| | | Avg. | 6.0 ± 2.4 |

In addition to the alveolar interstitial fluid, lymphatics also contain a significant amount of extraseptal filtrates from vessels outside the alveolar walls. This was illustrated by Nicolaysen, et al., Microvasc. Res. 9:29–37 (1975) who injected albumin tagged with Evans blue and followed the appearance of the dye in the lung interstitium. The dye appeared in the lymphatics within 10 minutes while the appearance of dye within the interstitium took approximately twice as long, indicating the presence of non-alveolar filtration. It was estimated by Gropper, et al., Federation Proc. 43:1032 (1984) that a minimum of 40% of the total lung lymph filtration was of non-alveolar origin. Thus, to account for non-alveolar dilution of the lymph, the concentration in the interstitial fluid is multiplied by 1.7. Table VII lists the calculated interstitial levels of α1AT while accounting for 40% extraseptal contribution and 84% plasma clearance.

TABLE VII

| Sheep # | Calc. Peak Interstitial Levels |
|---|---|
| 4 | 1.3 |
| 6 | 1.5 |
| 7 | 3.2 |
| Avg. | 2.0 ± 1.0 |

Example 5—Estimation of Human Dose from Sheep Data

The results of the α1AT deposited dose experiments and absorption experiments, described above, indicate that a protective level for humans of α1AT in interstitial fluid (approx. 6M, or 324 g/ml) may be achieved in humans using pulmonary administration of dry powder α1AT. In particular, extrapolating the sheep data to humans suggests that in order to augment interstitial levels of α1AT in deficient individuals to a protective level (i.e., to approx. 6M from 3.4 M in deficient individuals) a 70 kg human would need to inhale approximately 20 to 60 mg of α1AT per day for three days. After the three day therapy, the patent would then be able to inhale 10 to 20 mg per day to replace the α1AT transported out of the lungs and maintain the protective levels. This is substantially reduced from projected doses for liquid aerosol forms of 200 mg per day (see, Hubbard and Crystal, Lung Suppl:565–578 (1990). These estimated doses are approximated based upon average data. Appropriate dosages would likely vary from individual to individual depending upon the nature of the α1AT deficiency, i.e., acquired or genetic, as well as the base level of the individual.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A method of administering α1-antitrypsin to a patient, comprising:
    providing said α1-antitrypsin as a dry powder comprising aggregates of fine particles, wherein said fine particles have a mean particle size of from about 1 μm to about 5 μm and said aggregates have a mean size of from about 50 μm to about 600 μm, and wherein said agglomerates have a friability index of from about 10 to about 60;
    aerosolizing said dry powder composition; and
    administering from 1 mg to 80 mg of said aerosolized dry powder composition pulmonarily to said patient per day.

2. The method as recited in claim 1, comprising:
    dispersing an amount of the α1-antitrypsin dry powder in a gas stream to form an aerosol; and
    capturing the aerosol in a chamber suitable for subsequent inhalation by the patient.

3. The method as recited in claim 1, wherein in said providing step said α1-antitrypsin dry powder is greater than about 50% pure.

4. The method as recited in claim 1, wherein in said providing step said α1-antitrypsin dry powder is greater than about 90% pure.

5. The method as recited in claim 1, wherein in said providing step said α1-antitrypsin dry powder is greater than about 95% pure.

6. The method as recited in claim 1, wherein in said providing step said α1-antitrypsin dry powder is greater than about 99% pure.

7. The method of claim 1, wherein said aggregates are spherical in shape.

8. The method of claim 1, wherein said aggregates are formed with a nonaqueous solvent binding liquid.

9. The method of claim 8, wherein said nonaqueous solvent binding liquid comprises a fluorocarbon liquid.

10. The method of claim 9, wherein said fluorocarbon liquid is selected from the group consisting of perfluorodecalin and perfluorooctyl bromide.

11. The method as recited in claim 1, wherein said dispersible dry powder composition of α1-antitrypsin is from about 70% to about 90% pure.

12. A method of treating a patient deficient in α1-antitrypsin, comprising administering pulmonarily to said patient, a therapeutically effective amount of a α1-antitrypsin dry powder.

13. The method of claim 12, wherein said therapeutically effective amount comprises from about 1 to about 50 mg of α1-antitrypsin daily.

14. The method as recited in claim 12, wherein said therapeutically effective amount comprises from about 5 to about 25 mg of α1-antitrypsin daily.

15. The method as recited in claim 12, wherein said therapeutically effective amount comprises from about 10 to about 15 mg of α1-antitrypsin daily.

16. A method of treating a patient suffering from emphysema, comprising administering pulmonarily to said patient from 1 mg to 80 mg per day of a therapeutically effective amount of aerosolized dry powder α1-antitrypsin, wherein said powder comprises aggregates of fine particles, wherein said fine particles have a mean particle size of from about 1 μm to about 5 μm and said aggregates have a mean size of from about 50 μm to about 600 μm, and wherein said agglomerates have a friability index of from about 10 to about 60.

17. An apparatus for administering α1-antitrypsin to a patient, the apparatus comprising:
    a housing having a chamber disposed therein, said chamber containing an amount in the range from 1 mg to 80 mg of an α1-antitrypsin dry powder composition, said powder composition comprising aggregates of fine particles, wherein said fine particles have a mean particle size of from about 1 μm to about 5 μm and said aggregates have a mean size of from about 50 μm to about 600 μm, and wherein said agglomerates have a friability index of from about 10 to about 60;
    a gas pressure source fluidly connected to said chamber, for delivering a gas stream to said chamber to aerosolize said dry powder composition; and
    a means for delivering said aerosolized dry powder composition for inhalation by said patient, said means for delivering being fluidly connected to said chamber.

18. A method of administering α1-antitrypsin to a patient, comprising:
    providing said α1-antitrypsin as a dry powder, wherein the powder comprises particles having an aerodynamic diameter less than 5 μm;

aerosolizing said dry powder composition; and administering said aerosolized dry powder composition pulmonarily to said patient.

19. The method as recited in claim 18, comprising:

dispersing an amount of the α1-antitrypsin dry powder in a gas stream to form an aerosol; and capturing the aerosol in a chamber suitable for subsequent inhalation by the patient.

20. The method as recited in claim 18, wherein in said providing step said α1-antitrypsin dry powder is greater than about 50% pure.

21. The method as recited in claim 18, wherein in said providing step said α1-antitrypsin dry powder is greater than about 90% pure.

22. The method as recited in claim 18, wherein in said providing step said α1-antitrypsin dry powder is greater than about 95% pure.

23. The method as recited in claim 18, wherein in said providing step said α1-antitrypsin dry powder is greater than about 99% pure.

24. The method of claim 18, wherein in said providing step said α1-alantitrypsin dry powder comprises aggregates of fine particles, wherein said fine particles have a mean particle size of from about 1 μm to about 5 μm and said aggregates have a mean size of from about 50 μm to about 600 μm, and wherein said agglomerates have a friability index of from about 10 to about 60.

25. The method of claim 24, wherein said aggregates are spherical in shape.

26. The method of claim 24, wherein said aggregates are formed with a nonaqueous solvent binding liquid.

27. The method of claim 26, wherein said nonaqueous solvent binding liquid comprises a fluorocarbon liquid.

28. The method of claim 27, wherein said fluorocarbon liquid is selected from the group consisting of perfluorodecalin and perfluorooctyl bromide.

29. The method as recited in claim 24, wherein said dispersible dry powder composition of α1-antitrypsin is from about 70% to about 90% pure.

30. A method of treating a patient deficient in α1-antitrypsin, comprising administering pulmonarily to said patient, a therapeutically effective amount of a α1-antitrypsin dry powder comprising particles having an aerodynamic diameter less than 5 μm.

31. The method of claim 30, wherein said therapeutically effective amount comprises from about 1 to about 50 mg of α1-antitrypsin daily.

32. The method as recited in claim 30, wherein said therapeutically effective amount comprises from about 5 to about 25 mg of α1-antitrypsin daily.

33. The method as recited in claim 30, wherein said therapeutically effective amount comprises from about 10 to about 15 mg of α1-antitrypsin daily.

34. A method of treating a patient suffering from emphysema, comprising administering pulmonarily to said patient a therapeutically effective amount of aerosolized dry powder α1-antitrypsin, wherein the powder comprises particles having an aerodynamic diameter less than 5 μm.

35. An apparatus for administering α1-antitrypsin to a patient, the apparatus comprising:

a housing having a chamber disposed therein, said chamber containing an amount of an α1-antitrypsin dry powder composition, wherein the powder comprises particles having an aerodynamic diameter less than 5 μm;

a gas pressure source fluidly connected to said chamber, for delivering a gas stream to said chamber to aerosolize said dry powder composition; and a means for delivering said aerosolized dry powder composition for inhalation by said patient, said means for delivering being fluidly connected to said chamber.

36. A respirable α1-antitrypsin powder comprising α1-antitrypsin particles having an aerodynamic diameter less than 5 μm.

37. A powder as in claim 36, wherein said α1-antitrypsin dry powder is greater than about 50% pure.

38. A powder as in claim 36, wherein said α1-antitrypsin dry powder is greater than about 90% pure.

39. A powder as in claim 36, wherein said α1-antitrypsin dry powder is greater than about 95% pure.

40. A powder as in claim 36, wherein said α1-antitrypsin dry powder is greater than about 99% pure.

41. A powder as in claim 36, wherein said α1-antitrypsin dry powder comprises aggregates of fine particles, wherein said fine particles have a mean particle size of from about 1 μm to about 5 μm and said aggregates have a mean size of from about 50 μm to about 600 μm, and wherein said agglomerates have a friability index of from about 10 to about 60.

42. A powder as in claim 41, wherein said aggregates are spherical in shape.

43. A powder as in claim 41, wherein said aggregates are formed with a nonaqueous solvent binding liquid.

44. A powder as in claim 43, wherein said nonaqueous solvent binding liquid comprises a fluorocarbon liquid.

45. A powder as in claim 44, wherein said fluorocarbon liquid is selected from the group consisting of perfluorodecalin and perfluorooctyl bromide.

46. A powder as in claim 43, wherein said dispersible dry powder composition of α1-antitrypsin is from about 70% to about 90% pure.

* * * * *

UNITED STATES PATENT AND TRADEMARK OFFICE
CERTIFICATE OF CORRECTION

PATENT NO. : 5,993,783
DATED : November 30, 1999
INVENTOR(S) : Mohammed Eljamal et al.

It is certified that error appears in the above-identified patent and that said Letters Patent is hereby corrected as shown below:

Title page,
Item [63], Related U.S. Application Data, after "5,780,014" insert -- , which is a continuation-in-part of U.S. Application No. 08/423,515, filed April 14, 1995, now abandoned --

Signed and Sealed this

Seventeenth Day of May, 2005

JON W. DUDAS
*Director of the United States Patent and Trademark Office*